United States Patent
Nutt et al.

(10) Patent No.: US 6,449,331 B1
(45) Date of Patent: Sep. 10, 2002

(54) COMBINED PET AND CT DETECTOR AND METHOD FOR USING SAME

(75) Inventors: Robert E. Nutt; Ronald Nutt, both of Knoxville, TN (US)

(73) Assignee: CTI, Inc., Knoxville, TN (US)

( * ) Notice: Subject to any disclaimer, the term of this patent is extended or adjusted under 35 U.S.C. 154(b) by 0 days.

(21) Appl. No.: 09/756,820

(22) Filed: Jan. 9, 2001

(51) Int. Cl.$^7$ ............................................... G01T 1/166
(52) U.S. Cl. ..................................... 378/19; 250/363.04
(58) Field of Search ........................... 378/4, 19, 98.8; 250/363.02, 363.03, 363.04, 370.06, 370.08, 370.09

(56) References Cited

U.S. PATENT DOCUMENTS

| | | | |
|---|---|---|---|
| 5,289,008 A | * 2/1994 | Jaszczak et al. | 250/363.03 |
| 5,376,795 A | * 12/1994 | Hasegawa et al. | 250/363.04 |
| 5,550,379 A | * 8/1996 | Schreck et al. | 250/369 |
| 6,329,657 B1 | * 12/2001 | Watson et al. | 250/363.03 |

OTHER PUBLICATIONS

David W. Townsend, et al., in their paper "The SMART Scanner: A Combined PET/CT Tomograph for Clinical Oncology," presented at the 1998 IEEE Nuclear Science Symposium and Medical Imaging Conference in Toronto, Canada, on Nov. 12–14, 1998.

P. E. Kinahan, et al., "Attenuation Correction for a Combined 3D PET/CT Scanner," Med. Phys. 25 (10), 2046–53 (Oct. 1998).

* cited by examiner

Primary Examiner—David P. Porta
(74) Attorney, Agent, or Firm—Pitts & Brittian, P.C.

(57) ABSTRACT

A combined positron emission tomography (PET) and computed tomography (CT) detector mounted on a single support on the same gantry of a combined PET and CT scanner. The common detector includes an array of scintillator crystals or pixels with each pixel mated to a photodetector. The photodetector is connected to discrete event circuitry, which provides discrete event information to the combined PET and CT scanner. Also, the photodetector is connected to integrating circuitry, which provides integrated count rate information to the CT scanner when the discrete event information is not adequate. By using a common detector, the registration of the PET image with the CT image is improved, less components are mounted on the gantry, the overall size of the gantry is reduced, resulting in a shorter tunnel and less rotating mass, and CT performance is enhanced by providing means for selecting the energy level of the x-rays to be detected.

15 Claims, 7 Drawing Sheets

COMBINED PET AND CT DETECTOR AND METHOD FOR USING SAME

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to a detector which has the capability of operating in either positron emission tomography (PET) or x-ray computerized tomography (CT) mode. More specifically, it relates to a combined PET and CT scanner detector which allows a PET scanner and a CT scanner to utilize common detectors, resulting in better registration of the metabolic PET image with the anatomical CT image, fewer components in the gantry, and a reduction of the overall size and mass of the gantry.

2. Description of the Related Art

Various techniques are used for medical imaging. PET and CT are popular in radiology because of their ability to non-invasively study physiological processes and structures within the body. To better utilize PET and CT, recent efforts have been made to combine the two scanners into a single machine. This allows for better registration of the metabolic PET image with the anatomic CT image. The combined scanners share space on the same gantry, but use separate detectors, and associated hardware.

Positron Emission Tomography (PET) is a nuclear imaging technique used in the medical field to assist in the diagnosis of diseases. PET allows the physician to examine the whole patient at once by producing pictures of many functions of the human body unobtainable by other imaging techniques. In this regard, PET displays images of how the body works (physiology or function) instead of simply how it looks. PET is considered the most sensitive, and exhibits the greatest quantification accuracy, of any nuclear medicine imaging instrument available at the present time. Applications requiring this sensitivity and accuracy include those in the fields of oncology, cardiology, and neurology.

In PET, short-lived positron-emitting isotopes, referred to as radiopharmaceuticals, are injected into a patient. When these radioactive drugs are administered to a patient, they distribute within the body according to the physiologic pathways associated with their stable counterparts. For example, the radiopharmaceutical $^{18}$F-labeled glucose, known as fluorodeoxyglucose or "FDG", can be used to determine where normal glucose would be used in the brain. Other radioactive compounds, such as $^{11}$C-labeled glucose, $^{13}$N-labeled ammonia and $^{15}$O-labeled water, are used to study such physiological phenomena as blood flow, tissue viability, and in vivo brain neuron activity.

As the FDG or other radiopharmaceutical isotopes decay in the body, they discharge positively charged particles called positrons. Upon discharge, the positrons encounter electrons, and both are annihilated. As a result of each annihilation event, gamma rays are generated in the form of a pair of diametrically opposed photons approximately 180 degrees (angular) apart. By detecting these annihilation "event pairs" for a period of time, the isotope distribution in a cross section of the body can be reconstructed. These events are mapped within the patient's body, thus allowing for the quantitative measurement of metabolic, biochemical, and functional activity in living tissue. More specifically, PET images (often in conjunction with an assumed physiologic model) are used to evaluate a variety of physiologic parameters such as glucose metabolic rate, cerebral blood flow, tissue viability, oxygen metabolism, and in vivo brain neuron activity.

Mechanically, a PET scanner consists of a bed or gurney and a gantry, which is typically mounted inside an enclosure with a tunnel through the center, through which the bed traverses. The patient, who has been treated with a radiopharmaceutical, lies on the bed, which is then inserted into the tunnel formed by the gantry. The gantry is rotated (either physically or electronically simulated with a stationary ring) around the patient as the patient passes through the tunnel. The rotating gantry contains the detectors and a portion of the processing equipment. Signals from the rotating gantry are fed into a computer system where the data is then processed to produce images.

The PET scanner detectors are located around the circumference of the tunnel. The detectors use a scintillator to detect the gamma rays. Suitable material used for the scintillator includes, but is not limited to, either lutetium oxyorthosilicate (LSO) or bismuth germanate (BGO). The light output from the scintillator is in the form of light pulses corresponding to the interactions of gamma rays with the crystal. A photodetector, typically a photomultiplier tube (PMT) or an avalanche photodiode, detects the light pulses. The light pulses are counted and the data is sent to a processing system.

Another known tomography system is computed axial tomography (CAT, or now also referred to as CT, XCT, or x-ray CT). In CT, an external x-ray source is caused to be passed around a patient. Detectors around the patient then respond to the x-ray transmission through the patient to produce an image of the area of study. Unlike PET, which is an emission tomography technique because it relies on detecting radiation emitted from inside the patient, CT is a transmission tomography technique which utilizes a radiation source external to the patient. CT provides images of the internal structures of the body, such as the bones, whereas PET provides images of the functional aspects of the body, usually corresponding to an internal organ or tissue.

The CT scanner uses a similar mechanical setup as the PET scanner. However, unlike the pairs of PET scanner detectors required to detect the gamma rays from an annihilation event, the CT scanner requires detectors mounted opposite an x-ray source. In third-generation computed tomography systems, the CT detectors and x-ray source are mounted on diametrically opposite sides of a gantry which is rotated around the patient as the patient traverses the tunnel.

The x-ray source emits a fan-shaped beam of x-rays which pass through the patient and are received by an array of detectors. As the x-rays pass through the patient, they are attenuated as a function of the densities of objects in their path. The output signal generated by each detector is representative of the electron densities of all objects between the x-ray source and the detector.

The CT detectors can utilize scintillator crystals which are sensitive to the energy level of the x-rays. Multiple light pulses produced by each scintillator crystal as it interacts with the x-rays are integrated to produce an output signal which is related to the number of the x-rays sensed by the scintillator crystal. The individual output signals are then collectively processed to generate a CT image. Other detectors can be used in CT tomographs. For example, a solid state silicon diode can be used to detect the low energy x-rays directly.

The medical images provided by the PET scanner and CT scanner are complementary, and it is advantageous to have images from both types of scans. To be most useful, the PET and CT images need to be overlaid or co-registered such that the functional features in the PET images can be correlated with the structural features, such as bones, tumors, and lung tissue, in the CT images. The potential to combine functional and anatomical images is a powerful one, and there has been significant progress in the development of multi-modality image co-registration and alignment techniques. However, with the exception of the brain, the re-alignment of images from different modalities is not straightforward or very accurate, even when surface markers or reference points are used. To this end, it is desirable to incorporate PET and CT scanners into a single gantry, thereby allowing the images to be taken sequentially within a short period of time and overcoming alignment problems due to internal organ movement; variations in scanner bed profile, and positioning of the patient for the scan.

In recent years, there has been considerable progress in the development of techniques to co-register and align functional and anatomical images. For example, David W. Townsend, et al., in their paper "The SMART Scanner: A Combined PET/CT Tomograph for Clinical Oncology," presented at the 1998 IEEE Nuclear Science Symposium and Medical Imaging Conference in Toronto, Canada, on Nov. 12–14, 1998, described a combined PET and CT tomograph. In this paper, the authors showed that a spiral CT scanner could be combined with a PET tomograph with the components mounted on a common rotational support within a single gantry. The PET and CT components could be operated either separately or in combined mode. The combined PET and CT scanner described in this article required a patient tunnel of 110 centimeters in order to accommodate the independent PET and CT components.

In P. E. Kinahan, et al., "Attenuation Correction for a Combined 3D PET/CT Scanner," Med. Phys. 25 (10), 2046–53 (October 1998), the authors described their conception of a combined PET and CT scanner, in which the independent scanners were mounted on a rotating gantry. They identified the advantages of such an arrangement as including the application of CT-based attenuation correction to the PET scan and the use of CT data directly in the image reconstruction process.

Independent PET and CT detectors use numerous components which occupy space in the rotating gantry. This duplication of detectors results in inaccuracies in registration of the PET image with the CT image, a deeper patient tunnel, increased number of components in the gantry, increased mass on the gantry, and potentially higher cost.

Therefore, it is an object of the present invention to provide a common detector for a PET scanner and a CT scanner.

It is a further object of the present invention to improve the overlay registration of individual PET and CT images.

It is a further object of the present invention to reduce the number of components on the gantry and to reduce the depth of the tunnel.

Another object of the present invention is to detect a multitude of discrete, x-ray generated, scintillator events and provide count rate information for processing into a CT image by integrating the charge information from the multitude of x-ray events.

Still another object of the present invention is to count the individual x-ray events for a specified time to provide digital count rate information gathered from the common detector to generate a CT image.

BRIEF SUMMARY OF THE INVENTION

In accordance with the teachings of the present invention, a common detector provides data which is processed to generate a PET image and a CT image. The common detector is mounted on a single support within the same gantry. The common detector includes an array of scintillator crystals or pixels, each pixel having a photodetector feeding both discrete event circuitry and integrating circuitry, both of which feed a processing system. A PET image and a CT image are generated sequentially by scanning a patient twice, once after the patent is injected with a radiopharmaceutical and once with an x-ray source rotated about the patient.

The common detector operates in three modes. The first mode of operation is as a standard PET detector, which detects individual gamma rays. When operating in this mode, the photodetector feeds a charge amplifier, which outputs a signal proportional to the energy level of a single detected gamma ray. In this mode, a fast timing signal is also derived. The second mode of operation is as a standard CT detector, which detects multiple x-rays over a short sample period. When operating in this mode, the photodetector feeds an integrator, which outputs an integrated signal proportional to the number of x-rays detected for the sample period. In the third mode of operation, the detector senses individual x-rays and outputs discrete event information which is processed into a CT image. In this mode, the photodetector feeds a fast amplifier, an energy discriminator, and a counter/timer circuit, which outputs a digital signal proportional to the number of x-rays detected in a preset time interval.

By using a common detector, the registration of the PET image with the CT image is improved, fewer components are mounted on the gantry, the overall size and mass of the gantry is reduced, and the tunnel the patient has to enter is shorter, reducing patient anxiety and claustrophobic effect. Also, the third mode of operation provides a digital signal to the CT scanner, which results in improved stability when compared to the analog method of the second mode of operation. tHE third mode also enables an output based on a specified range of x-ray energy, which provides an improvement in CT image contrast.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
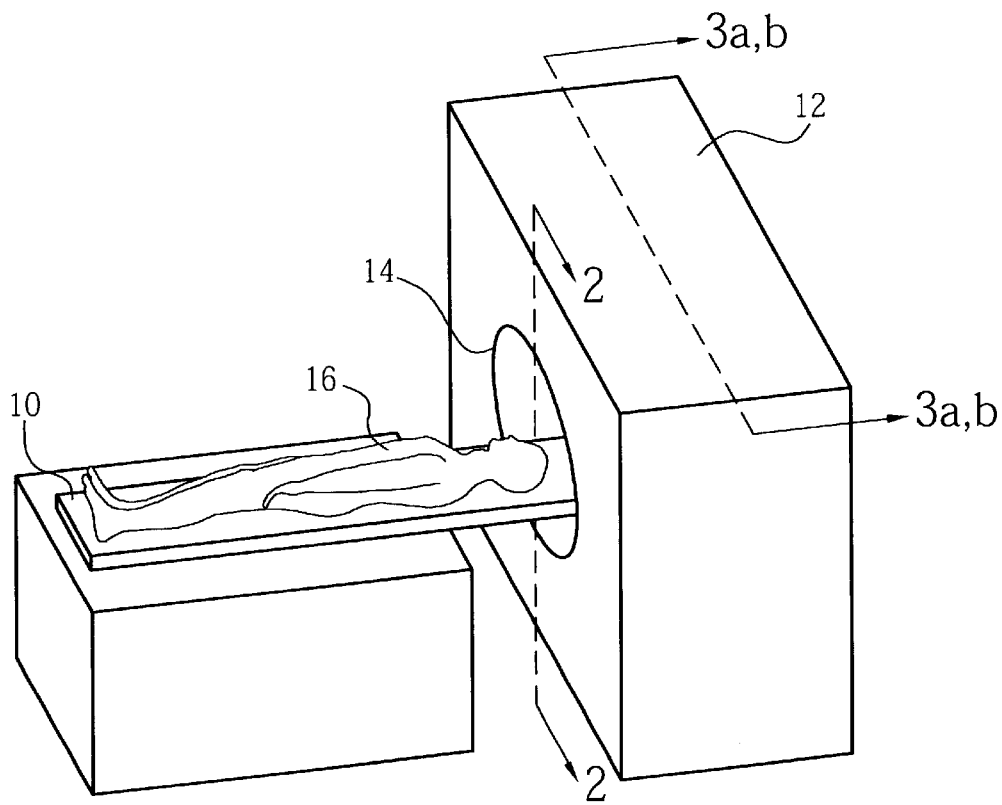
FIG. 1 is a pictorial view of the combined PET and CT scanner, including a patient platform or bed.

Referring to FIG. 1, a combined positron emission tomography (PET) and computed tomography (CT) imaging system (a combined PET and CT scanner) is shown as including an enclosure 12 for a rotating gantry representative of a third generation CT scanner. The enclosure 12 has a tunnel 14 through which the patient 16, who lies on the bed 10, traverses.

Figure 2:
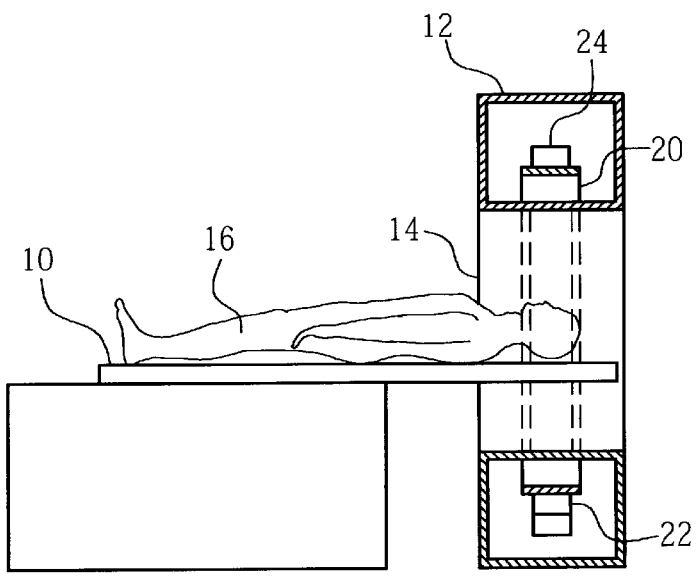
FIG. 2 illustrates a cut-away section of the combined PET and CT scanner showing a side view of the combined PET and CT detector.

FIG. 2 illustrates a combined PET and CT scanner with a detector 24 constructed in accordance with the present invention. A plurality of detectors 24 are mounted around the circumference of the gantry 20. At one or more points on the circumference, one or more x-ray sources 22 are mounted. While scanning, the gantry 20 is rotated around the patient 16, who is traversing the tunnel 14. The PET scan and the CT scan are taken sequentially without requiring the patient to get off the bed 10.

Figure 3A:
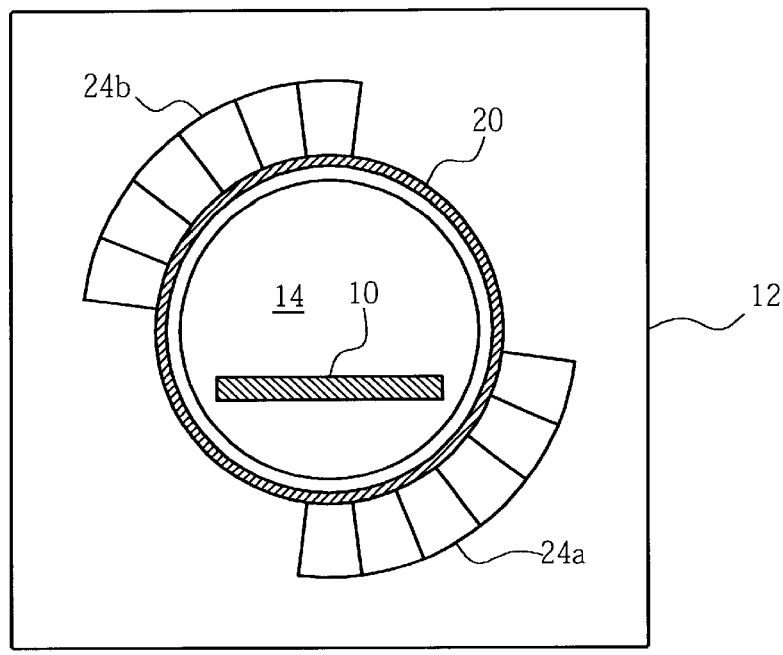
FIG. 3a illustrates a cut-away section of the combined PET and CT scanner showing a front view of the gantry with the combined PET and CT detectors in the PET scanning configuration.
Figure 3B:
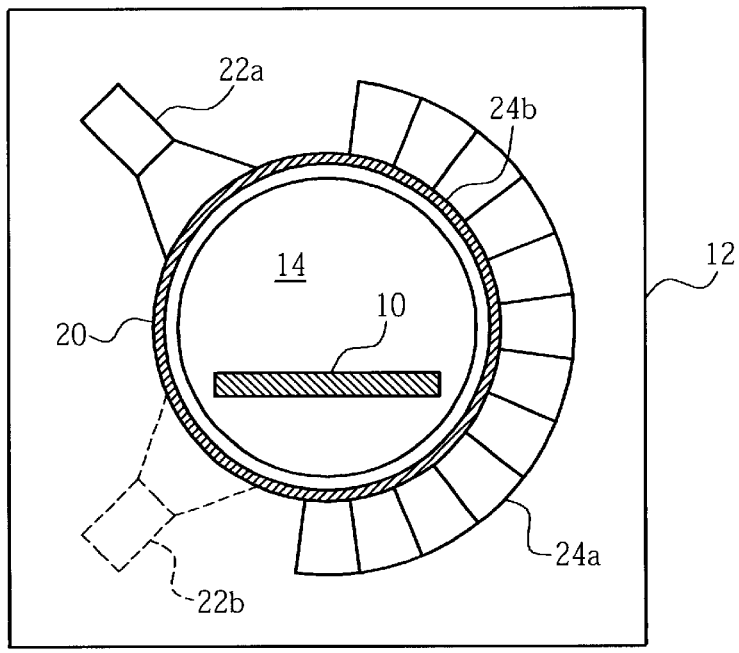
FIG. 3b illustrates a cut-away section of the combined PET and CT scanner showing a front view of the gantry with the combined PET and CT detectors in the CT scanning configuration.

FIG. 3a and 3b show the arrangement of the arrays of the detectors 24 when the combined PET and CT scanner is operated in its two modes, first as a PET scanner and second as a CT scanner. FIG. 3a shows the configuration of the arrays of the detectors 24 when the combined PET and CT scanner is operated as a PET scanner. In this mode of operation, the two arrays of detectors 24 are mounted diametrically opposite each other on the gantry. When a PET scan is performed, a pair of detectors 24 produces. a pair of output signals that represent an annihilation event resulting from the decay of the radiopharmaceutical injected into the patient 16. The locations of the sensing detectors establishes the line of response (LOR).

FIG. 3b shows the preferred embodiment of the detectors 24 when the combined PET and CT scanner is operated as a CT scanner. In this mode of the array of detectors 24b is rotated around the circumference of the gantry 20, from their position as shown in FIG. 3a to the location shown in FIG. 3b, which is adjacent to the other array of detectors 24a. x-ray source 22a is exposed and is diametrically opposite the array of detectors 24a. If a second x-ray source 22b is used, it is located diametrically opposite the array of detectors 24b, which is the array of detectors that was rotated from its original position opposite the array of detectors 24a. When a CT scan is performed, each detector 24 produces an output signal that represents the impinging of x-rays from its corresponding x-ray source 22.

While this description of the CT scanning mode is the preferred embodiment, those skilled in the art will recognize that other alternatives for performing a CT scan can be used without interfering with the objects and advantages of the present invention. As an example, an alternative CT scanner would have the x-ray sources 22 mounted off the gantry 20, and instead of the gantry 20 rotating around the patient 16, the x-ray beam is caused to rotate around the patient' striking a reflector on the gantry 20 and being reflected through the patient and onto the array of detectors 24.

The signals from the detectors 24 are independently processed to produce a PET image and a CT image, respectively. These images are combined for a composite PET and CT image. The detector 24 allows PET and CT images to be acquired from a single device, resulting in improved registration of the PET image with the CT image, resulting in fewer components in the gantry 20, a reduction of size and mass of the gantry 20, a shorter tunnel 14, and improvement in CT performance.

Figure 4:
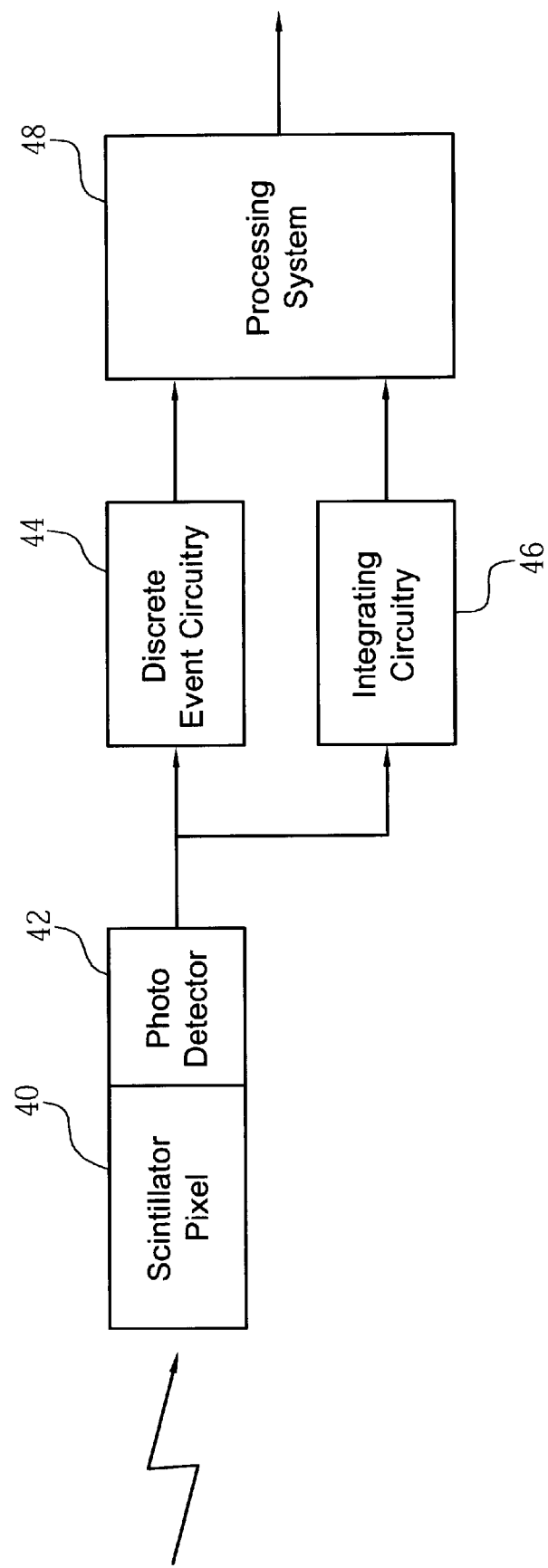
FIG. 4 shows a block diagram of a common PET and CT detector.

Referring to FIG. 4, the detector 24 includes a plurality of scintillator crystals or pixels 40, each of which is optically coupled to a photodetector 42. The output of each photodetector 42 feeds discrete event circuitry 44 and integrating circuitry 46. The outputs of the discrete event circuitry 44 and the integrating circuitry 46 feed the processing system 48, of the combined PET and CT scanner, which generates the PET and CT images. In the preferred embodiment, the signal path for both PET and CT scanning is from each scintillator pixel 40 to the photo-detector 42 to the discrete event circuitry 44 to the processing system 48. However, when the desired signal rate cannot be reached, the signal path for CT scanning is from each scintillator pixel 40 to the photo-detector 42 to the integrating circuitry 46 to the processing system 48, resulting in a detector output based on integrating scintillator events.

Figure 5A:
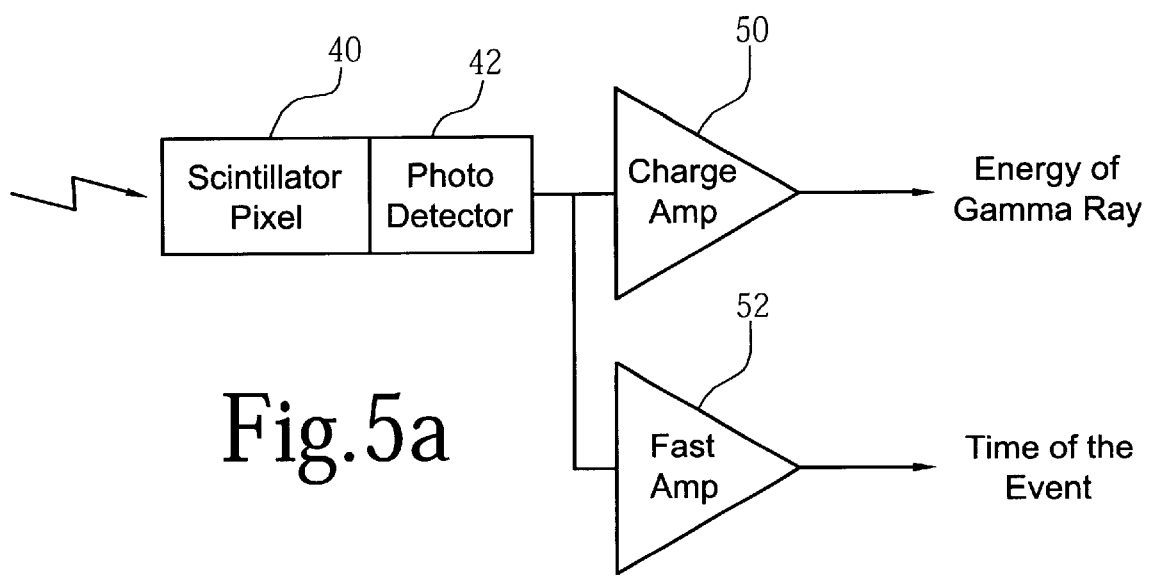
FIG. 5a shows a block diagram of a common PET and CT detector when operated in the standard PET mode.
Figure 5B:
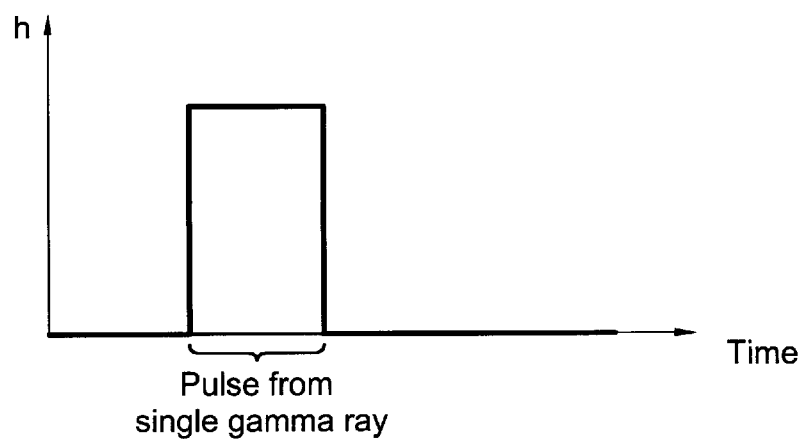
FIG. 5b shows a graph of the output for a single detected gamma ray.
Figure 6A:
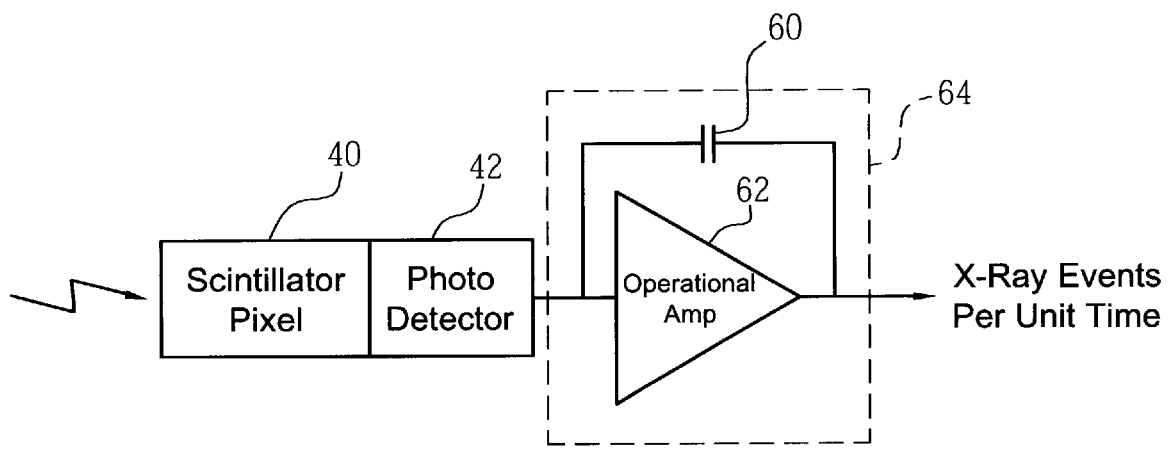
FIG. 6a shows a block diagram of a common PET and CT detector when operated in the standard CT mode.
Figure 7:
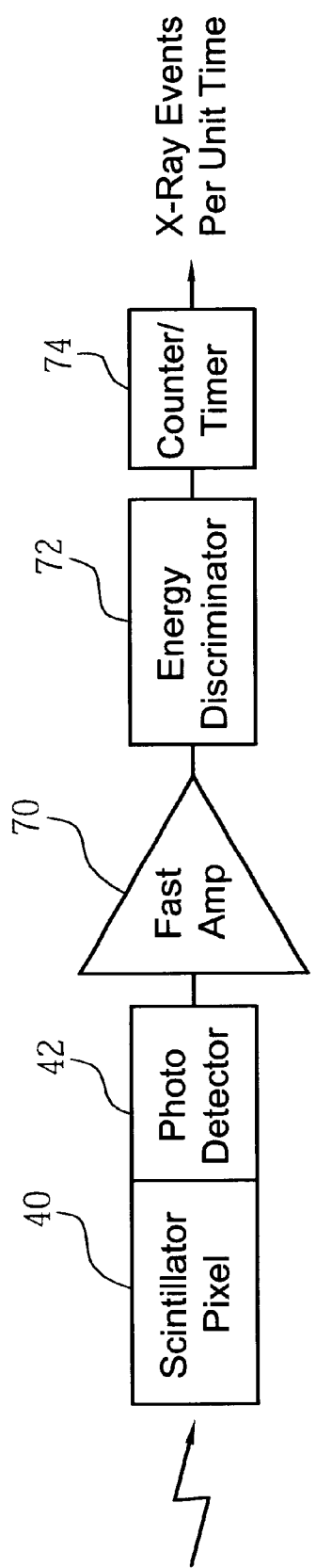
FIG. 7 shows a block diagram of a common PET and CT detector when operated in the discrete event mode for CT scanning.

FIG. 5a, 6a, and 7 provide more detailed information on the discrete event circuitry 44 and integrating circuitry 46. FIG. 5a shows the configuration for a PET scanner using discrete event circuitry 44. A gamma ray, produced from an annihilation event resulting from the decay of the radiopharmaceutical injected into the patient 16, interacts with a scintillator crystal or pixel 40 and is sensed by the photo-detector 42. The output of the photodetector 42 feeds a charge amplifier 50 which produces an output waveform as shown in FIG. 5b, where a pulse is generated with a duration of approximately 100 nanoseconds to 1 microsecond and a height h proportional to the energy level of the single gamma ray. The output of the photodetector 42 also feeds a fast amplifier 52 which is used to provide information on the time of the event. Those skilled in the art will recognize that other configurations may be used for processing the output of the photodetector 42 without interfering with the objects and advantages of the present invention.

Figure 6B:
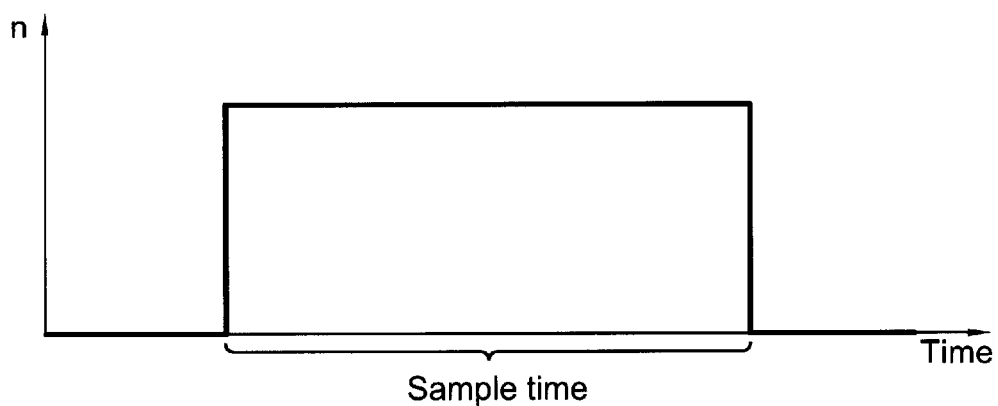
FIG. 6b shows a graph of the output for multiple x-rays for a sample period.

FIG. 6a shows the configuration for a CT scanner using integrating circuitry 46. A plurality of x-rays emitted from an x-ray source 22 interact with a scintillator crystal or pixel 40 over a short sample period. These x-ray interactions are sensed by a photodetector 42, which outputs a signal to an integrator 64. Integrator 64, in one embodiment, is an operational amplifier 62 with a feedback capacitor 60. The output waveform of the integrator 64 is shown in FIG. 6b. The generated pulse, shown in FIG. 6b, has a duration of approximately 10 microseconds to several milliseconds and an amplitude n proportional to the number of x-ray events sensed for the sample period. Those skilled in the art will recognize that other configurations may be used for processing the output of the photodetector 42 without interfering with the objects and advantages of the present invention.

FIG. 7 shows the configuration for a CT scanner using discrete event circuitry 44. An x-ray emitted from the x-ray source 22 interacts with a scintillator crystal or pixel 40 and is sensed by a photodetector 42. The output of the photodetector 42 feeds a fast amplifier 70, which outputs to an energy discriminator 72, which outputs to a counter/timer 74. The energy discriminator 72 filters out signals that do not correspond to x-rays within a specified energy level range. The output from the discrete event circuitry 44 shown in FIG. 7 is a digital signal proportional to the number of x-ray events sensed per preset time period. Those skilled in the art will recognize that other configurations may be used for processing the output of the photodetector 42 without interfering with the objects and advantages of the present invention.

FIG. 4 shows the preferred embodiment of the detector 28 and includes, for PET scanning, the discrete event circuitry 44 shown in FIG. 5a and, for CT scanning, the integrating circuitry 46 shown in FIG. 6a and the discrete event circuitry 44 shown in FIG. 7. For CT scanning, the integrating circuitry 46 is used when the desired count rate exceeds the capabilities of the detector 28 using the discrete event circuitry 44.

Figure 8:
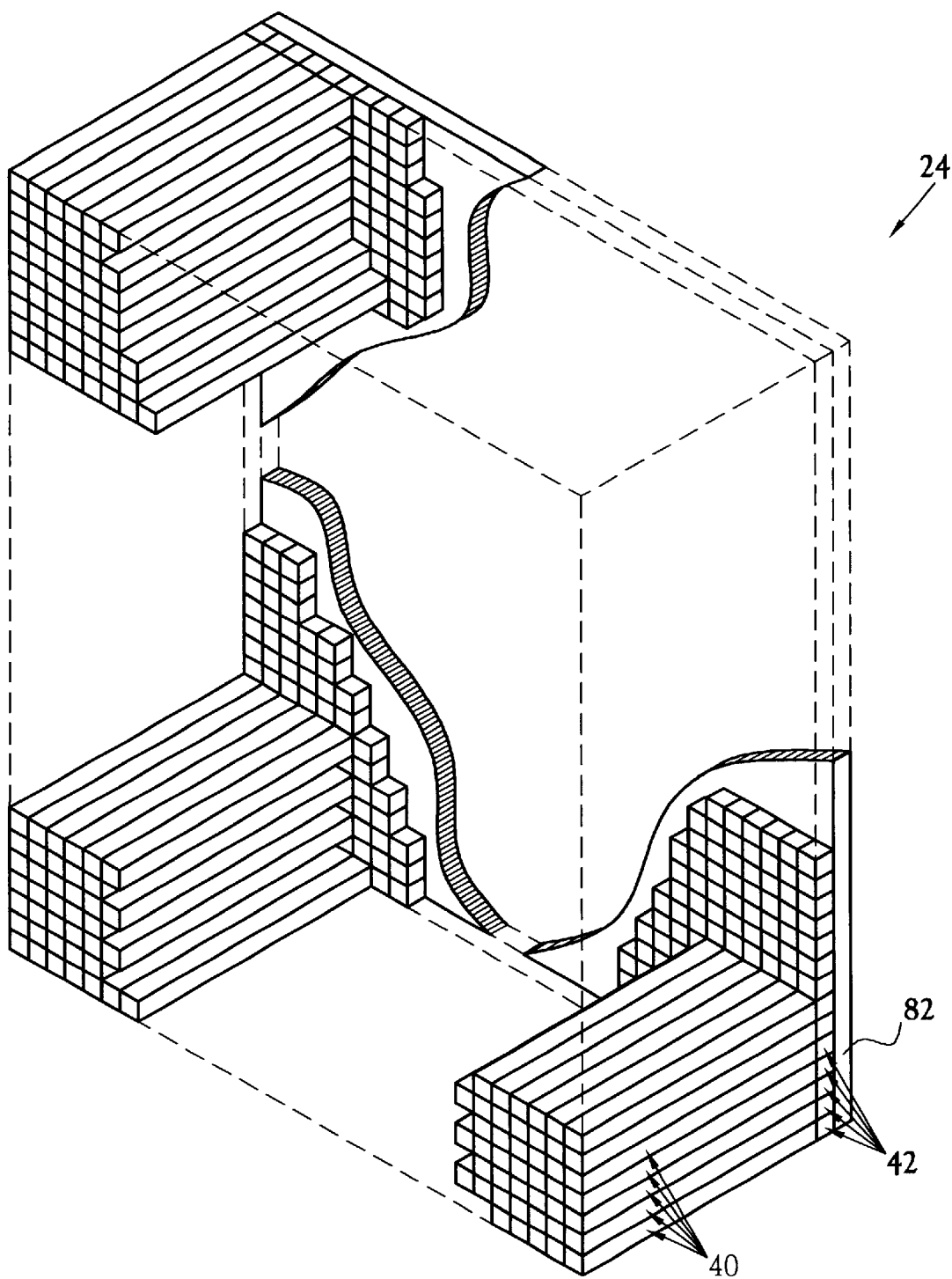
FIG. 8 illustrates the detector, which includes an array of scintillator pixels attached to photodetectors mounted on a circuit board.

FIG. 8 shows the preferred embodiment of the detector 24, the scintillator crystals or pixels 40 are crystals of LSO or similar scintillator material, each fastened to one of a plurality of photodetectors 42 which are mounted on a circuit board 82. LSO is a desirable scintillator material because it has a high light output for both gamma rays and x-rays, and it has a short decay rate which permits a high count rate. Those skilled in the art will recognize that other crystals can be used without interfering with the objects and advantages of the present invention. The surface of the detector 24 is divided into an array of 1.5 millimeter square pixels, each one forming a scintillator pixel 40. An array of scintillator pixels or crystals 40 that is approximately 40 centimeters by 52 centimeters can have an array of 268 by 335 pixels, for a total of 89,780 scintillator pixels 40.

Each scintillator crystal or pixel 40 is optically coupled to a photodetector 42. Typically, the photodetector 42 is a photomultiplier tube or an avalanche photodiode. The scintillator pixels 40 are optically isolated from each other by a reflective material, such as Teflon tape. Each scintillator pixel 40 is epoxied to a photodetector 42 with an optically transparent epoxy. The photodetectors 42 are mounted on a circuit board 82 which also contains the discrete event circuitry 44 and/or the integrating circuitry 46. Those skilled in the art will recognize that any of several methods of detecting scintillator events and that any of several methods of isolating pixels from each other and coupling the pixels to the photodetectors can be used without interfering with the objects and advantages of the present invention.

Each scintillator crystal or pixel 40 has a maximum output signal count rate related to the inverse of the scintillator decay time. For a scintillator crystal with a 40 nanosecond decay, such as LSO, the maximum count rate without substantial error would be approximately 10 million counts per second. This count rate is adequate for all PET imaging, but not for most CT imaging. Accordingly, the discrete event circuitry 44 of FIG. 5a is used for all PET imaging, and the discrete event circuitry 44 of FIG. 7 is used for CT imaging where the count rate is adequate. The integrating circuitry 46 of FIG. 6a is used for those cases where a greater count rate is needed for CT imaging. With the integrating circuitry 46, the individual pulses from the photodetector 42 are not identified as in the discrete event circuitry 44, but simply added to the signal by the integrating circuitry 46.

From the foregoing description, it will be recognized by those skilled in the art that a detector 24 offering advantages over the prior art has been provided. Specifically, a detector 24 is provided for the operation of a combined PET and CT scanner to perform functional (PET) and anatomical (CT) imaging in patients. By using a common detector, the registration of the PET image with the CT image is improved, fewer components are mounted on the gantry 20, the overall size and mass of the gantry 20 is reduced, and the tunnel 14 the patient has to enter is shorter, reducing patient anxiety and claustrophobic effect. The discrete event mode of operation for CT scanning provides a digital signal, which results in improved stability when compared to the analog method of the integrating mode of operation and provides an improvement in CT image contrast. Also, CT scanner performance is improved by providing a means for selecting the energy level of the x-rays to be detected.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, we claim:

1. A detector for sensing radiation emitted from a positron emission tomography source (PET source) and from a computed tomography source (CT source), said detector comprising:

a scintillator crystal responsive to radiation emitted from a PET source and responsive to radiation emitted from a CT source;

a photodetector in optical communication with said scintillator crystal, said photodetector responsive to said scintillator crystal;

a first discrete event circuit for PET scanning including a charge amplifier connected to said photodetector, said charge amplifier having an output corresponding to a gamma ray energy level, and a fast amplifier connected to said photodetector, said fast amplifier having an output corresponding to a detection time; and a second discrete event circuit for CT scanning, said second discrete event circuit including said fast amplifier connected to said photodetector, an energy discriminator connected to said fast amplifier, and a counter/timer responsive to said energy discriminator and having an output proportional to a count rate corresponding to a plurality of x-rays detected from the CT source within a specified energy level range sensed over a preset time period.

2. The detector of claim 1 wherein said scintillator crystal is formed from a lutetium oxyorthosilicate crystal.

3. The detector of claim 1 wherein said photodetector is either one of a photomultiplier tube and an avalanche photodiode.

4. The detector of claim 1 further including an integrating circuit for CT scanning, said integrating circuit connected to said photodetector.

5. The detector of claim 1 wherein said scintillator crystal is one of a plurality of crystals arranged in an array, each one of said plurality of crystals forming a pixel.

6. A method for detecting radiation emitted from a computed tomography source (CT source), said method comprising the steps of:

(a) sensing radiation from a CT source as sensed radiation with a scintillator crystal and a photodetector in optical communication with said scintillator crystal;

(b) processing said sensed radiation, wherein said step of processing is accomplished with a discrete event circuit including a fast amplifier connected to said photodetector;

an energy discriminator connected to said fast amplifier, said energy discriminator filtering out a signal corresponding to an x-ray energy level outside a specified range; and a counter/timer responsive to said energy discriminator and having an output proportional to a count rate corresponding to a plurality of x-rays detected from the CT source within a specified energy level range sensed over a preset time period.

7. The method of claim 6 wherein said step of processing said sensed radiation from the CT source comprises the step of determining a count rate, wherein the CT source emits a plurality of x-rays and said count rate corresponds to the number of said plurality of x-rays sensed over a preset time period.

8. The method of claim 6 wherein said step of processing said sensed radiation from the CT source comprises the step of filtering, wherein the CT source emits a plurality of x-rays and said step of filtering applies to said plurality of x-rays which have an energy level outside a specified range.

9. The method of claim 8 wherein said step of processing said sensed radiation from the CT source further comprises, after said step of filtering, the step of counting said plurality of x-rays which have an energy level within said specified range sensed over a sample period.

10. The method of claim 6 wherein said step of processing said sensed radiation from the CT source comprises the step of counting, wherein the CT source emits a plurality of x-rays and said step of counting applies to said plurality of x-rays sensed over a sample period.

11. A detector for sensing radiation emitted from a computed tomography source (CT source), said detector comprising:

a scintillator crystal responsive to radiation emitted from a CT source;

a photodetector in optical communication with said scintillator crystal, said photodetector responsive to said scintillator crystal;

a fast amplifier connected to said photodetector;

an energy discriminator connected to said fast amplifier, said energy discriminator filtering out a signal corresponding to an x-ray energy level outside a specified range; and a counter/timer responsive to said energy discriminator and having an output proportional to a count rate corresponding to a plurality of x-rays detected from the CT source within a specified energy level range sensed over a preset time period.

12. The detector of claim 11 wherein said scintillator crystal is one of a plurality of crystals arranged in an array, each one of said plurality of crystals forming a pixel.

13. A detector for sensing radiation resulting from a positron emission tomography source (PET source) and from a computed tomography source (CT source), said detector comprising:

a means for sensing radiation from a PET source and from a CT source with a single device;

a means for determining a gamma ray energy level and a time of event from the PET source; and a means for determining a number of x-ray events per a specified period from the CT source.

14. A method for detecting radiation emitted from a positron emission tomography source (PET source) and from a computed tomography source (CT source), said method comprising the steps of:

(a) sensing radiation with a single device from a PET source and a CT source;

(b) for said PET source, determining a gamma ray energy level and a time of detection; (c) for said CT source, determining a count rate corresponding to a plurality of x-rays sensed over a preset time period.

15. A detector for sensing radiation emitted from a positron emission tomography source (PET source), and from a computed tomography source (CT source), said detector comprising:

a scintillator crystal responsive to radiation emitted from a PET source and responsive to radiation emitted from a CT source, said scintillator crystal formed of lutetium oxyorthosilicate;

a photodetector in optical communication with said scintillator crystal, said photodetector responsive to said scintillator crystal;

a first discrete event circuit for PET scanning including a charge amplifier connected to said photodetector, said charge amplifier having an output corresponding to a gamma ray energy level, and a fast amplifier connected to said photodetector, said fast amplifier having an output corresponding to a detection time;

a second discrete event circuit for CT scanning, said second discrete event circuit including said fast amplifier connected to said photodetector, an energy discriminator connected to said fast amplifier, and a counter/timer responsive to said energy discriminator and having an output proportional to a count rate corresponding to a plurality of x-rays detected from the CT source within a specified energy level range sensed over a preset time period; and an integrator for CT scanning, said integrator in communication with said photodetector.

* * * * *

UNITED STATES PATENT AND TRADEMARK OFFICE
CERTIFICATE OF CORRECTION

PATENT NO.     : 6,449,331 B1
DATED          : September 10, 2002
INVENTOR(S)    : Robert E. Nutt and Ronald Nutt It is certified that error appears in the above-identified patent and that said Letters Patent is hereby corrected as shown below:

<u>Title page,</u>
Item [73], indicate the Assignees as:
-- Concorde Microsystems, Inc., Knoxville, Tenn., and CTI PET Systems, Inc., Knoxville, Tenn. --

Signed and Sealed this

Eighteenth Day of March, 2003

JAMES E. ROGAN
*Director of the United States Patent and Trademark Office*